United States Patent [19]
Koch

[11] Patent Number: 5,980,804
[45] Date of Patent: Nov. 9, 1999

[54] METHOD FOR FORMING A CUSTOM MOLDED CERVICAL CAP

[76] Inventor: James P. Koch, 211 Sargent Rd., Brookline, Mass. 02146

[21] Appl. No.: 08/985,012

[22] Filed: Dec. 4, 1997

Related U.S. Application Data

[63] Continuation of application No. 08/462,071, Jun. 5, 1995, abandoned, which is a continuation-in-part of application No. 07/989,089, Dec. 11, 1992, Pat. No. 5,510,064.

[51] Int. Cl.[6] .......................... B29C 33/42; B29C 45/76
[52] U.S. Cl. ............................... 264/222; 264/DIG. 30; 128/841
[58] Field of Search ............................... 425/2; 264/40.1, 264/222, 259, 250, 255, 267, 268, 275, 334, 511, DIG. 30; 128/841, 898, 899, 918, DIG. 23; 604/330, 331

[56] References Cited

U.S. PATENT DOCUMENTS

| | | |
|---|---|---|
| 2,295,062 | 9/1942 | Townsend ............................... 128/841 |
| 2,764,975 | 10/1956 | Greenberg ............................... 128/841 |
| 2,818,064 | 12/1957 | Leff . | 
| 2,836,177 | 5/1958 | Sells . |
| 4,381,771 | 5/1983 | Gabbay ............................... 604/330 |
| 4,384,572 | 5/1983 | Goepp ............................... 128/841 |
| 4,517,970 | 5/1985 | Goepp et al. ............................... 128/841 |
| 4,543,949 | 10/1985 | Goepp et al. . |
| 5,510,064 | 4/1996 | Koch ............................... 264/40.1 |

Primary Examiner—Angela Ortiz
Attorney, Agent, or Firm—Fish & Richardson P.C.

[57] ABSTRACT

A method is provided of forming a cervical cap in situ, i.e., within a patient's body, which cap will substantially completely conform to the shape of the patient's cervix, allowing the cap to be left in place over an extended period of time. The method of the invention includes the steps of positioning a snugly fitting rim member around the patient's exocervix, mounting a shell member, having an aperture, onto the rim member such that the rim member, shell member and exocervix define a cavity, and injecting a curable material through the aperture to substantially fill the cavity. After the curable material is allowed to harden, the entire assembly is removed from the patient and the shell removed from the cured material.

30 Claims, 12 Drawing Sheets

METHOD FOR FORMING A CUSTOM MOLDED CERVICAL CAP

This is a continuation of Ser. No. 08/462,071, filed Jun. 5, 1995, now abandoned, which is a continuation-in-part of Ser. No. 07/989,089, filed Dec. 11, 1992, now U.S. Pat. No. 5,510,064.

BACKGROUND OF THE INVENTION

The invention relates to methods of forming cervical caps.

Cervical caps, i.e., cap-shaped devices which fit over a patient's cervix to prevent ingress of sperm into the patient's uterus, have long been used for contraception. Most of these devices are not custom molded to the shape of the individual patient's cervix, but are merely provided in several sizes. While many of these non-customized devices provide good contraception, they cannot be left in for extended periods of time, and typically must be removed after as little as 48 hours, making them hardly more convenient than diaphragm-type contraceptive devices.

Other cervical caps have been custom molded by a three-step process, typically requiring two visits to the clinician before the cap can be completed. This process involves the forming of a casting of the patient's cervix, typically using an alginate or polysiloxane impression material, making a plaster or stone model of the cervix using the casting, and thermoforming of a thermoplastic, e.g., a styrene-butadiene block copolymer, over the model. Custom forming of the cap allows the cap to conform very closely to the cervix, preventing buildup of fluids and reducing the possibility of infection, thus allowing the patient to keep the cap in place for much longer periods of time. For the cap to be left in place however, it is necessary to provide a one-way valve in the cap to allow egress of fluids from the uterus, while preventing any ingress of sperm. The design of some of these valves has reduced the contraceptive effectiveness of the cap.

Another method of forming a cervical cap in situ is disclosed in U.S. Pat. No. 4,007,249. According to this method, a layer of curable elastomeric material is applied directly to the surface of the patient's cervix and allowed to cure in place.

U.S. Pat. No. 5,123,424 proposes yet another method for forming a cervical cap in situ. In this method, a cervical cap, which includes a rim and a dome, is fitted to the patient's cervix, such that a gap is formed between the dome and cervix, and a biocompatible material is injected into the gap while the cap is in place. The finished cervical cap includes the cervical cap which was fitted to the patient and the biocompatible material, which bonds to the inner surface of the dome.

SUMMARY OF THE INVENTION

The invention features, in one aspect, a method of forming a cervical cap in situ, i.e., within a patient's body. The custom molded cap thus formed will substantially completely conform to the shape of the patient's cervix, allowing the cap to be left in place over an extended period of time. The method is easily performed, and typically requires only a single visit to the clinician.

The method of the invention includes the steps of positioning a snugly fitting rim member around a patient's exocervix, mounting a shell member, having an aperture, onto the rim member such that the rim member, shell member and exocervix define a cavity, and injecting a curable material through the aperture to substantially fill the cavity. After the curable material is allowed to harden, the entire assembly (rim, shell and curable material) is removed from the patient and the shell is removed from the cured material. The finished cap (formed from the rim and cured material) may then be used by the patient.

In preferred embodiments, the rim member is formed of a resilient biocompatible elastomeric material, preferably silicone rubber, and includes one or more ridges on its inner surface so that the rim positively grips the exocervix. It is further preferred that the shell member be translucent, to enable the clinician to observe when the cavity is substantially filled, and that the shell include a grip portion extending from its outer surface to allow the shell to be easily maneuvered into place and the assembly removed from the patient.

In another embodiment, the method includes the steps of positioning a snugly fitting rim member around the patient's exocervix, injecting a curable material over the exocervix such that it bonds to the entire circumference of the rim and covers the entire surface of the exocervix that is within the circumference of the rim. After the curable material has hardened, the cap, formed by the rim and curable material, may be removed from the patient's body. The cap will have an irregular outer surface. If a smooth surface is desired, the outer surface may be built up with additional curable material, e.g., by placing a shell member, partially filled with curable material and having an aperture so that excess material can escape, over the outer surface of the cap.

In another aspect, the method of the invention includes the steps of positioning a snugly fitting rim member around the patient's exocervix, providing a shell member having an aperture and containing an excess of a curable material, and mounting the shell member on the rim member. The excess curable material extrudes out of the aperture, the curable material is allowed to harden, and the shell member, rim and curable material are removed from the patient. The shell member may then be removed from the curable material, and the finished cap formed from the rim and curable material used by the patient.

In another aspect, the method of the invention includes the steps of positioning a snugly fitting rim member around the patient's exocervix, providing a shell member having a plurality of tubes extending therefrom, and mounting the shell member on the rim member such that the rim member, shell member and exocervix define a cavity and the tubes are in fluid communication with the cavity. The patient's cervix is then positioned in the shell member by providing a seal on all but one of the tubes to prevent air flow, inserting a syringe in the unsealed tube, and pulling a vacuum with the syringe, causing the patient's cervix to be drawn into the shell member. The cervical cap is formed by removing the seal from the sealed tubes and injecting a curable material through one of the tubes until the cavity is full. Preferably, the shell member and tubes are transparent, so that the clinician can observe that the cavity is full when material enters the tube(s) other than the one through which material is being injected. After the curable material has been allowed to harden, the entire assembly (rim, shell and curable material) is removed from the patient and the shell member is removed from the cured material. Preferably, the tails formed by the material inside the tubes are then removed, after which the finished cap (formed from the rim and the cured material) may be used by the patient.

In preferred embodiments, a spacer member includes two tubes extending therefrom, and the tubes are stabilized by the spacer member which maintains them in substantially fixed spaced relation. It is also preferred that the tubes extend outwardly from the shell member a sufficient distance so that they may be accessed by the clinician from outside the patient's body.

In all of the embodiments using a shell member (both those in which the shell member includes an aperture and those in which the shell member includes a plurality of tubes), the shell member and rim member may be joined prior to being positioned around the patient's exocervix or, alternatively, the rim member may be mounted on the patient's exocervix, and the shell member then mounted on the rim member. The former sequence of steps is preferred for the embodiments in which the shell member includes a plurality of tubes, whereas the latter sequence is preferred in those embodiments in which the shell member includes an aperture.

In another aspect, the invention features a method of positioning a patient's exocervix. The method includes the steps of placing a cervical plunger on the exocervix, drawing a vacuum to draw the surface of the exocervix towards the inner surface of the cervical plunger, and then moving the cervical plunger to position the cervix. Preferably, the cervix is moved to a position in which it is exposed, approximately straight relative to the sides of the patient's vagina, and visible to the clinician. By utilizing this method, it is possible to easily position the patient's cervix for clinical procedures, e.g., for formation of a cervical cap according to the above methods, using a relatively non-invasive procedure.

In another aspect, the invention features a method and apparatus for measuring the diameter of the exocervix at the fornices vaginae, and the depth of the exocervix from the fornices vaginae to the apex of the exocervix. A ring gauge is provided, comprising a plurality of ring members having different diameters,.means for positioning a selected ring member on the patient's exocervix, e.g., a pair of elongated members adapted to be removably attached to an outer surface of the ring member, and a measuring means for measuring the depth of the exocervix, e.g., a measuring member moveably mounted on one of the elongated members. A ring member of a first diameter is selected and placed in the positioning means, and, using the positioning means, positioned on the patient's cervix. This is repeated, if necessary, with ring members having diameters different from the first diameter, until a ring member is selected which fits the patient's exocervix, thus determining the diameter of the patient's exocervix. To determine the depth of the patient's exocervix, the measuring means is adjusted, e.g., by moving the measuring member along the elongated member until the measuring member contacts the patient's exocervix and measuring the distance between the measuring member and the ring member when this occurs. This can be measured, for example, by providing a scale on a portion of the elongated member on which the measuring member is mounted.

In preferred embodiments, the methods of positioning and measuring the cervix are utilized prior to the methods of forming a cervical cap, to facilitate sizing and placement of the rim member and shell member.

In another aspect, the invention features a cervical cap formed using any of the above methods. In preferred embodiments, the cap includes a flow control means, e.g., a one-way valve, to allow egress of fluids from the uterus when the cap is in use in the patient's body. In one embodiment, the means comprises an aperture in the cap and a flutter valve, fused to the cap around the aperture.

In another aspect, the invention features a kit for use by a clinician in forming a custom cervical cap in situ in a patient's body. In one embodiment, the kit includes a rim member, a curable material, and a means for applying the curable material. In another embodiment, the kit further includes a shell member dimensioned to be mounted on the rim member. In another embodiment, the kit further includes a ring gauge and/or a cervical plunger. In preferred embodiments, the kit includes a plurality of rim members, having different inner diameters, such that a plurality of rim members can be tried on the patient until one is found which snugly fits the patient's exocervix, and a plurality of shell members, each shell member dimensioned to fit a corresponding rim member. Preferably, the inner diameters of the rim members are from about 22 to 32 mm; more preferably, about 10 rim members are provided, with inner diameters 1 mm apart, the smallest of the rim members having an inner diameter of about 22 mm. In preferred embodiments, the kit includes a plurality of ring members, having different inner diameters, such that a plurality of ring members can be tried on the patient until one is found which snugly fits the patient's exocervix thus indicating the size of the corresponding rim member. In a further preferred embodiment, the means for applying the cured material comprises a syringe, preferably dimensioned to extend out of the patient's body when in use. In the embodiment in which the kit includes a shell member, the shell member has the preferred features described with reference to the method. Preferably, in the embodiment in which the shell member has an aperture, the syringe has an angled tip to facilitate insertion into the aperture in the shell member. In the embodiment in which the shell member has a plurality of tubes, the syringe preferably has a tip sized for insertion into one of the tubes. The kit may also include a forceps, a large aperture vaginal speculum, a lateral vaginal speculum, and instructions for use of the kit.

Other features and advantages of the invention will be apparent from the Description of the Preferred Embodiments thereof, and from the claims.

BRIEF DESCRIPTION OF THE DRAWINGS

FIG. 1a shows a cross sectional view of the rim member shown in FIG. 1, taken along line 1a—1a.

FIG. 3a shows a cross-sectional view of the cap shown in FIG. 3, taken along line 3a—3a.

FIG. 14 shows a cross-sectional view of the handle shown in FIG. 13, taken along line 13a—13a.

DESCRIPTION OF THE PREFERRED EMBODIMENT

Figure 1:
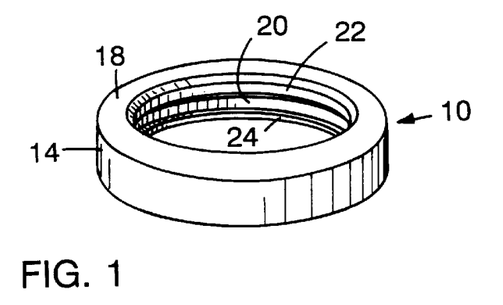
FIG. 1 shows a perspective view of a rim member according to one embodiment of the invention.
Figure 1A:
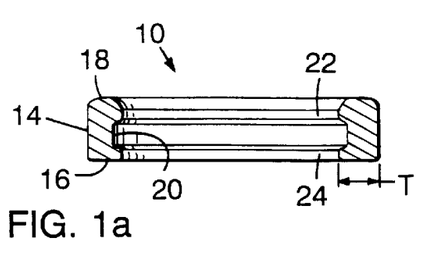
Figure 1B:
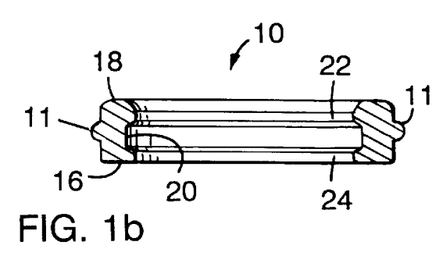
FIG. 1b shows a cross sectional view of a rim member according to an alternate embodiment of the invention.
Figure 2:
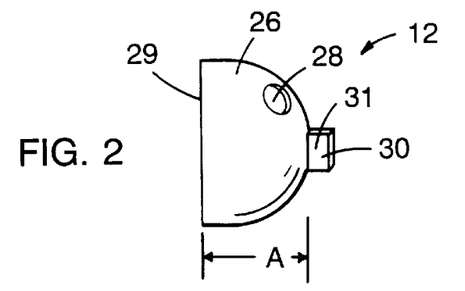
FIG. 2 shows a shell member according to one embodiment of the invention.

Preferred rim and shell members 10 and 12 are shown in FIGS. 1, 1a and FIG. 2, respectively. The preferred rim member 10 has a smooth, substantially vertical outer wall 14, a smooth, substantially horizontal lower wall 16, a convex upper surface 18, and a concave inner wall 20, defined by upper and lower ridges 22, 24. Ridges 22 and 24 extend around the entire circumference of the rim, to hold the rim firmly in place against the exocervix both during molding of the cap and during use of the finished cap. The rim member has an inner diameter which is sized to fit snugly over the exocervix of the patient who will use the finished cap, typically from about 20 to 35 mm, and an outer diameter of about 26 to 47 mm. The thickness of the rim (dimension T in FIG. 1A) preferably remains constant as the inner diameter is varied to fit the individual patient, i.e., rims having larger inner diameters have correspondingly larger outer diameters. The rim member is preferably made of a flexible, resilient biocompatible material, e.g., silicone. Suitable silicone elastomers are available from Dow Corning and Factor II.

A preferred shell member 12 includes hemispherical shell 26, aperture 28 disposed approximately halfway between the edge 29 and apex 31 of the hemisphere, and a gripping tab 30 disposed approximately at apex 31. Shell 26 is preferably formed of a material which is translucent or transparent, and which the curable material to be used will not adhere to, e.g., ethylene vinyl acetate or cellulose acetate. Preferably, the shell has a wall thickness of from about 1 to 3 mm, and has an inner diameter equal to (for a pressure fit) or slightly larger, e.g., about 1 to 3 mm larger, than the outer diameter of the rim member. Thus, for the preferred rim member dimensions, the shell will have an outer diameter of from 27 to 50 mm. The depth of the shell (dimension A in FIG. 2) is preferably determined for each patient. The preferred depth of the shell is from 2 to 10 mm greater than the protrusion of the patient's cervix from the rim when the rim is in place, or typically from about 10 to 25 mm total depth. Gripping tab 30 is preferably an approximately rectangular member, extending, in a plane approximately perpendicular to the plane of the edge of the hemisphere, from approximately the apex of the hemisphere. Aperture 28 preferably has a diameter of from about 4 to 8 mm.

Figure 3:
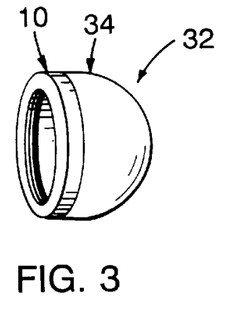
FIG. 3 shows a perspective view of a cap according to one embodiment of the invention.
Figure 3A:
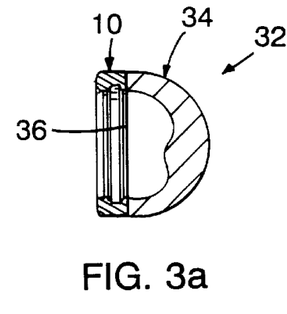

Following the method illustrated in FIGS. 4a–4d, or a similar method, a cap 32 is obtained as shown in FIGS. 3 and 3a. Cap 32 comprises rim 10, and dome 34 of biocompatible material bonded to surface 16 of rim 10. Materials suitable for use in forming dome 34 are those which will cure at the patient's body temperature, are biocompatible, and will adhere to the rim. Suitable materials include but are not limited to silicones and siloxanes. A suitable silicone is SILASTIC 382 silicone, available from Dow Corning. As shown in FIG. 3a, inner surface 36 of dome 34 is contoured to conform virtually identically to the surface of the patient's exocervix.

A method of forming a cervical cap in situ, according to a preferred embodiment, is shown in FIGS. 4a–4d.

Figure 4A:
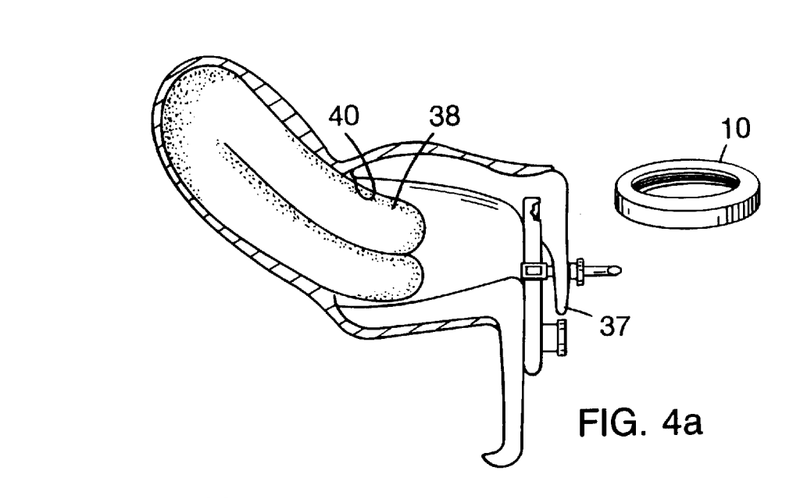
FIGS. 4a–4d show a method for forming a custom cervical cap according to one embodiment of the invention.

As shown in FIG. 4a, the patient's exocervix 38 is first exposed, typically by using a speculum 37 in a standard manner. A single speculum may not adequately expose the exocervix, in which case two speculums may be used, a standard vaginal speculum and a lateral vaginal speculum. The standard vaginal speculum will preferably have a large aperture, and the lateral speculum may need to be modified for use in the methods of the invention. To fully expose the exocervix may require a lateral speculum which is slightly wider and considerably longer than those which are commercially available, and which has straight rather than curved tips. If the clinician finds that the patient's cervix is not oriented so that it is facing approximately towards the clinician, the cervix can be so positioned by gently repositioning the uterus. A rim 10 of suitable size, i.e., one which fits exocervix 38 snugly, is selected, by trying different sizes, if necessary, and placed over the exocervix such that rim surface 18 is adjacent or near the fornices vaginae 40. The rim and/or cervix may be gently manipulated until this is achieved, and the protrusion of the exocervix from the rim is maximized. Forceps are generally used to position the rim. The tips of the forceps may be enlarged, e.g., with plastic blocks, to allow the rim to be more easily pressed onto the exocervix. The protrusion of the exocervix may then be measured, to determine the depth of the shell, as discussed above.

Figure 4B:
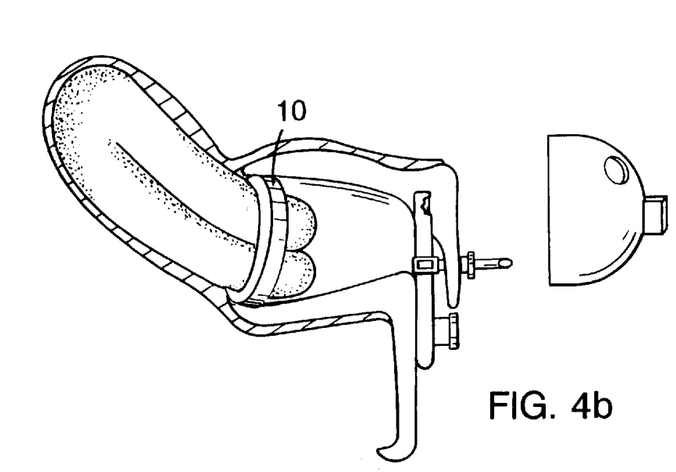
Figure 4C:
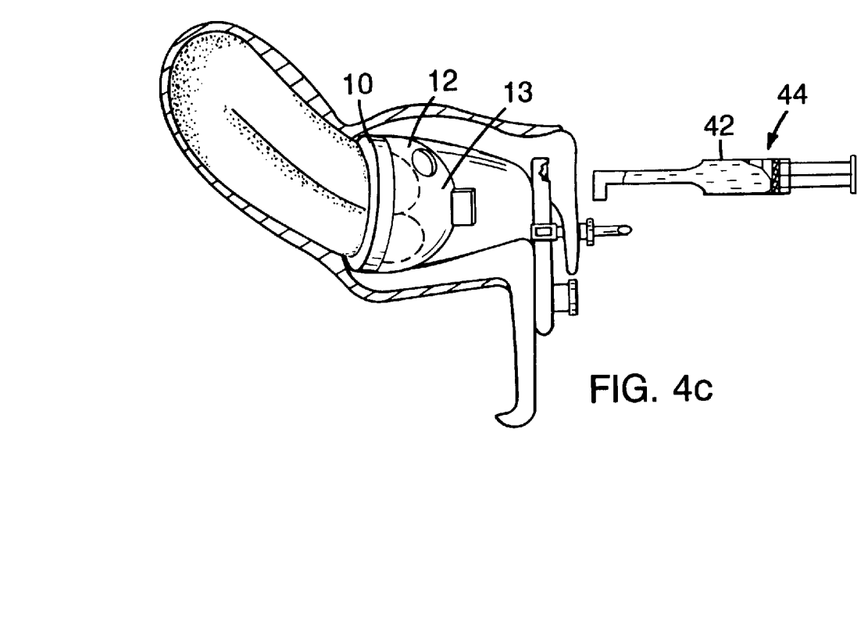

As shown in FIGS. 4b and 4c, a shell 12 having an inner diameter appropriate to fit the outer diameter of the selected rim is then fitted onto the rim, preferably snap-fit, such that shell 12, rim 10, and the patient's exocervix 38 define cavity 13. Because it is desirable that the shell only slide partially over the rim, and that the shell overlap the rim by a constant amount around the circumference of the rim, a flange 11 may be provided on the outer surface of the rim (see FIG. 1b) to act as a stop to prevent further movement of the shell. Curable material 42 is provided in a suitable dispensing device, e.g., a syringe 44 as shown. Syringe 44 preferably includes an angled tip 46, to allow the syringe to be easily inserted into aperture 28 in the shell without excessive movement of the syringe within the patient. A length of bent, semiflexible tubing may be attached to a standard syringe to form angled tip 46.

Figure 4D:
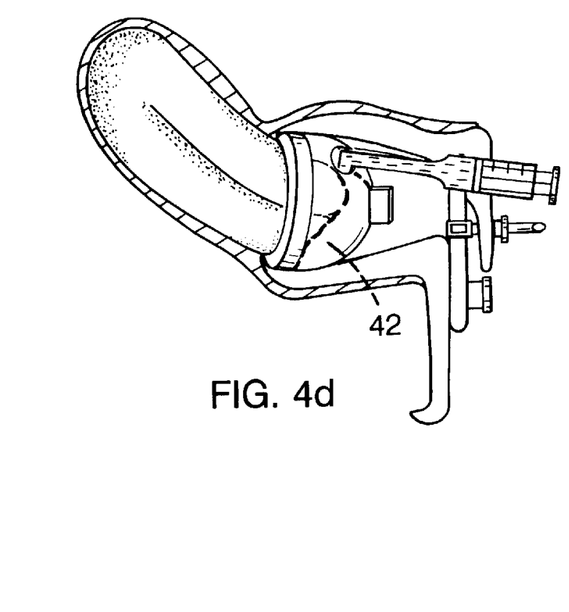

As shown in FIG. 4d, the curable material 42 is dispensed from the syringe 44, through the aperture 28 and into cavity 13, until cavity 13 is substantially or entirely filled. The degree to which the cavity is filled can be determined by observing the translucent shell. If an opaque shell is provided, the required volume of curable material can be easily calculated based on the volume of the shell.

After the curable material has been allowed to harden, typically from about 5 to 15 minutes, depending upon the setting time of the material used, the entire assembly (rim, shell, and cured material) is removed together (not shown) and the shell is removed from the cured material. The cap is then ready for use by the patient.

Figure 5A:
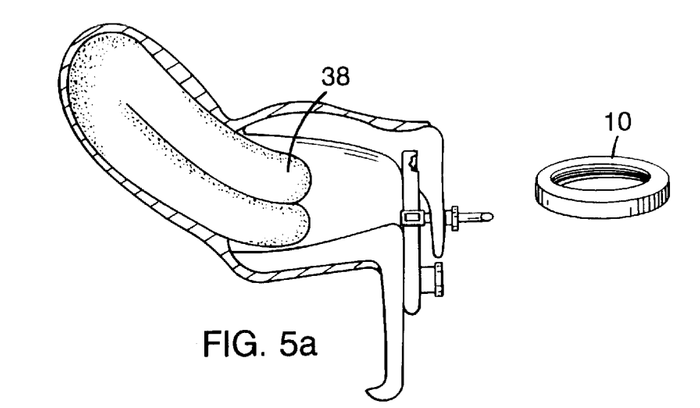
FIGS. 5a–5f show a method for forming a custom cervical cap according to an alternate embodiment of the invention.
Figure 5B:
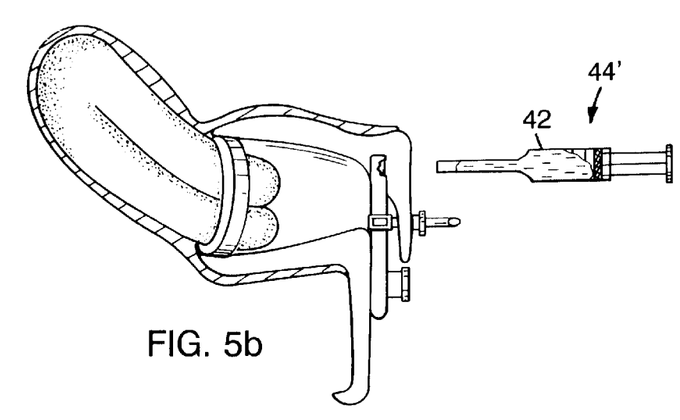
Figure 5C:
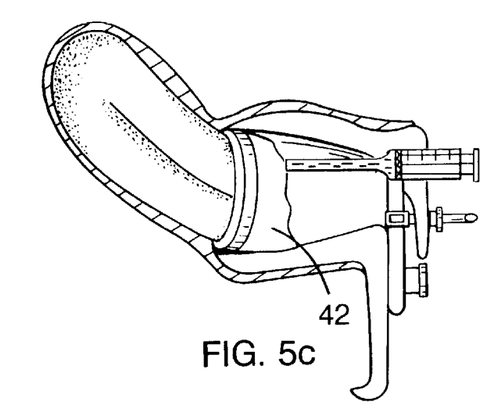
Figure 5D:
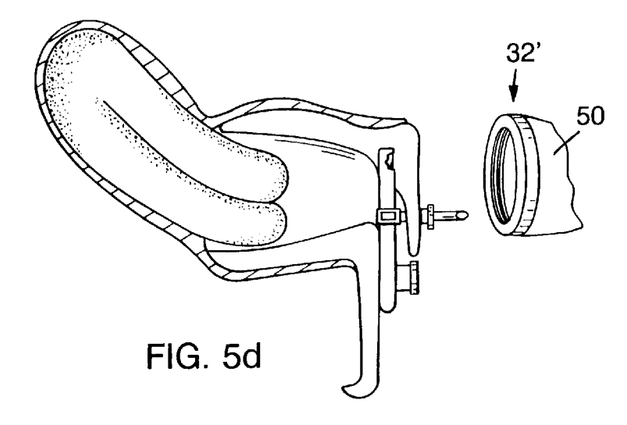
Figure 5E:
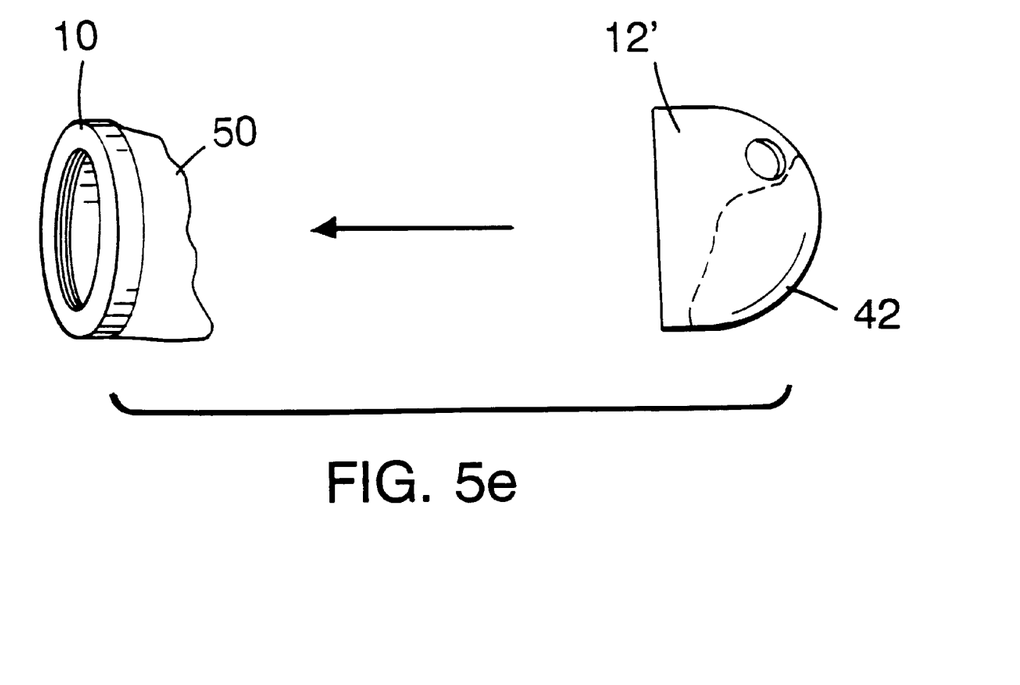
Figure 5F:
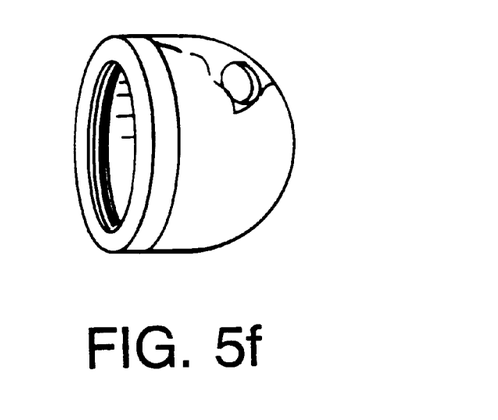
Figure 6A:
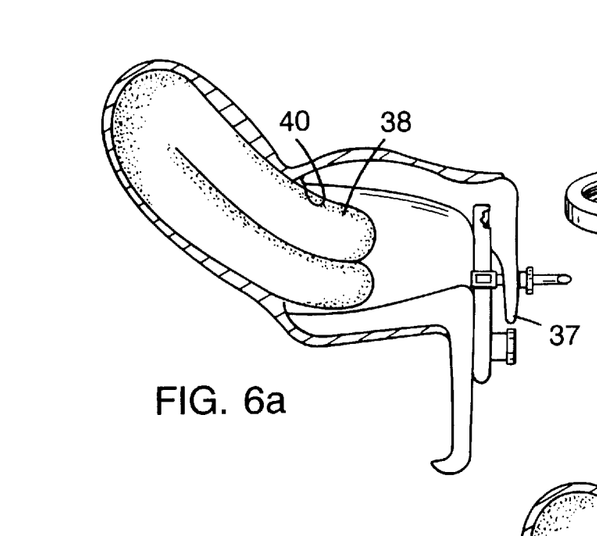
FIGS. 6a–6c show a method for forming a custom cervical cap according to another alternate embodiment of the invention.
Figure 6B:
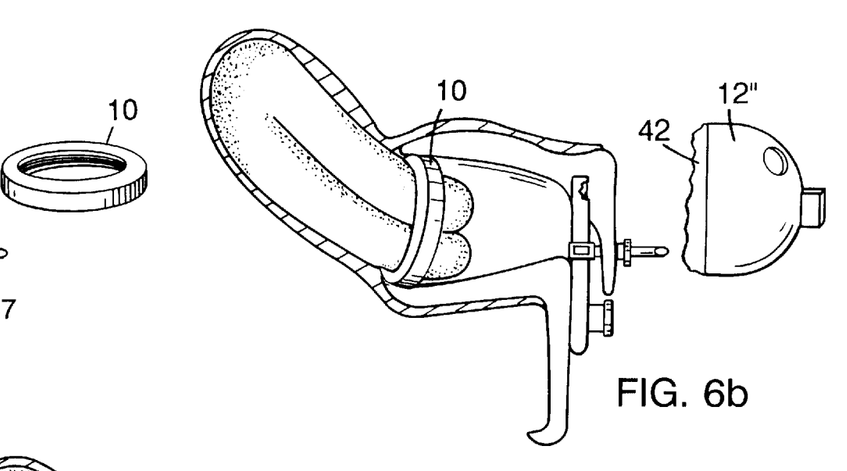
Figure 6C:
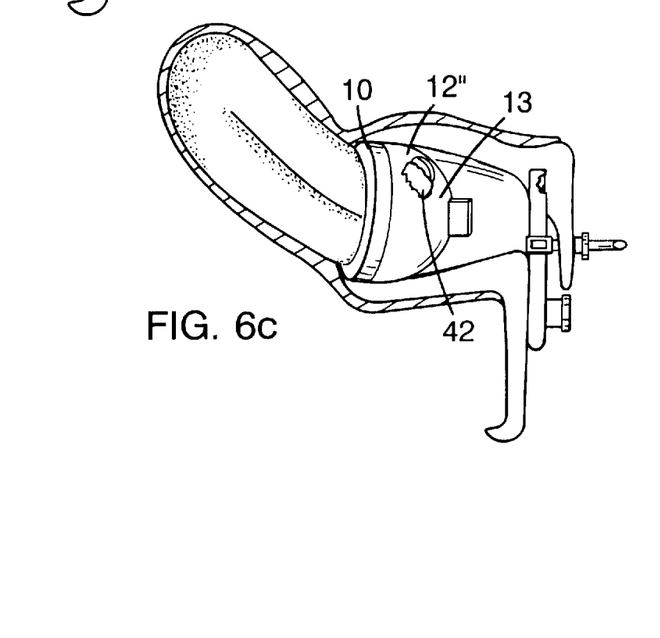

A method according to an alternate embodiment of the invention is shown in FIGS. 5a–5d. According to this method, a rim is again provided and the exocervix is exposed (FIG. 5a), and the rim is applied to the exocervix (FIG. 5b), as described above for the method shown in FIGS. 4a–4d. In this embodiment, however, curable material 42 in syringe 44' (FIG. 5b) is applied to the patient's exocervix, without a shell being applied to the rim (FIG. 5c). After the curable material has hardened, the cap 32', formed by the rim and the curable material bonded thereto, is removed from the patient (FIG. 5d). Cap 32' can then be used by the patient, if the irregular surface 50 is not objected to, provided that the entire area within the rim is covered with a continuous layer of hardened curable material. If desired, however, additional curable material can be applied to surface 50 of the cap, to make the surface smoother. This may be accomplished by partially filling shell member 12 with curable material 42, and placing the shell member over the cap (FIGS. 5e and 5f). After the curable material has hardened, the shell can be removed and the cap used.

Figure 7:
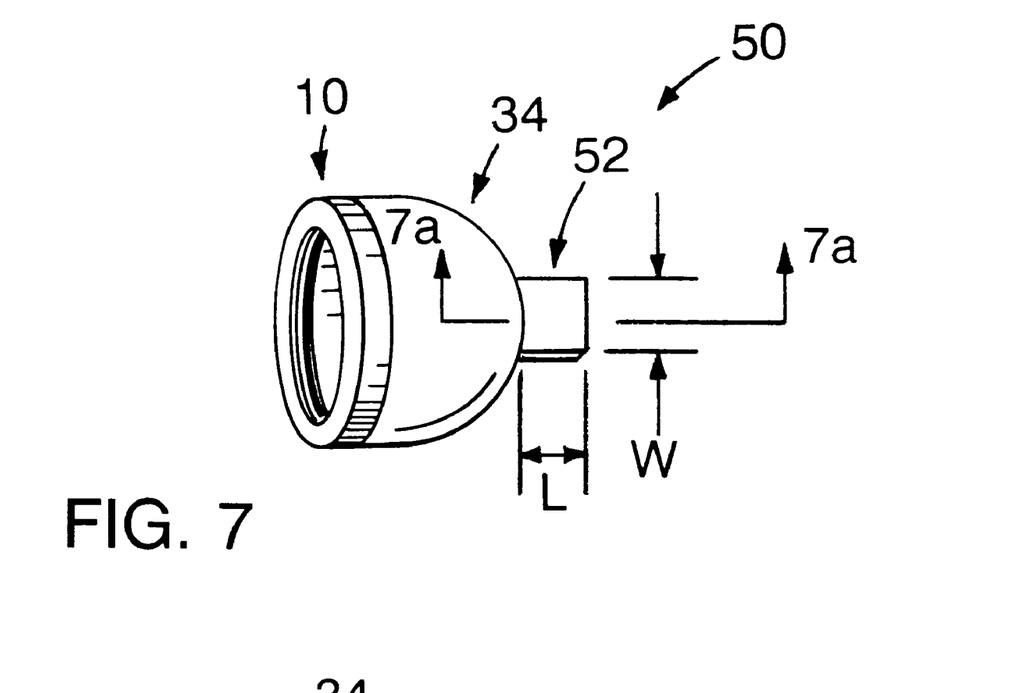
FIG. 7 is a front view, and FIG. 7a a side cross-sectional view, of a custom cervical cap including a valve according to one embodiment of the invention.
Figure 7A:
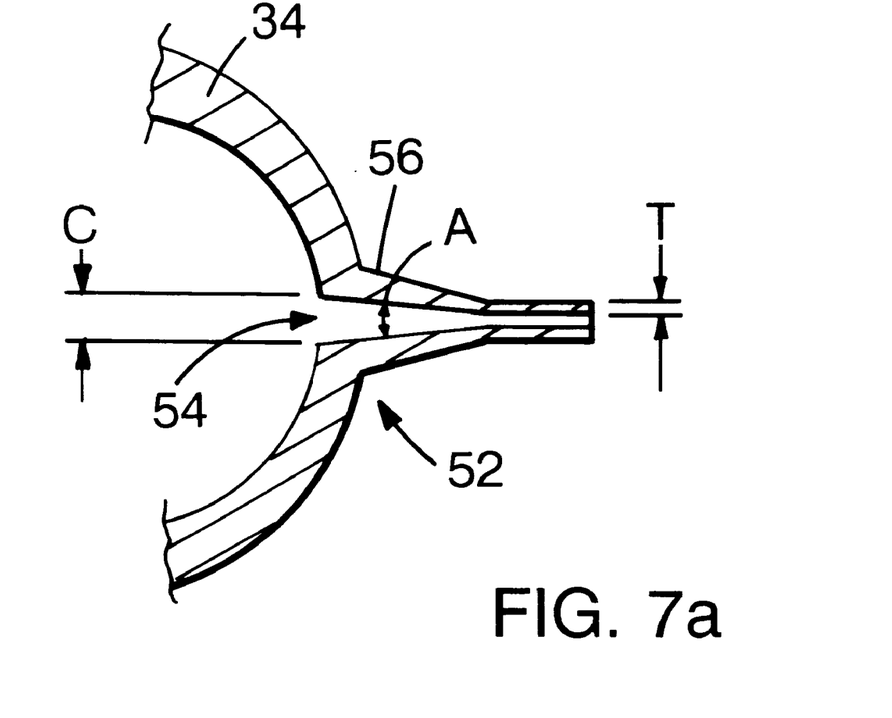

As shown in FIG. 7, the finished cap may include a valve 52. The valve is typically added to the cap after the cap is formed, although a valve could be included during molding, provided the custom fit of the cap is not interfered with. Valve 52, referred to herein as a "flutter valve", comprises a thin envelope of elastomeric material, open where it meets the cap and at its opposite end. Valve 52 extends from cap 50 near the apex of the cap, surrounding aperture 54 (see FIG. 7a). Prior to attachment of valve 52, aperture 54 is formed in cap 50. Valve 52 is then attached to cap 50 in an impermeable manner, preferably by fusing the two materials together, e.g., using a primer. Preferred dimensions of the valve shown in FIGS. 7 and 7a are approximately as follows: W=10 to 15 mm, L=20 to 30 mm, angle A=30 to 45 degrees. Aperture 54 in cap 52 preferably has a diameter C of about 2 to 10 mm. The wall thickness T of the valve is preferably about 0.5 to 1 mm. the opening at the end of the valve is preferably 1 mm or less. The valve may, however, have any dimensions which allow egress of fluid from the uterus while preventing ingress of sperm. The valve need not be a flutter valve, as shown, but could be, e.g., a long, thin tube of a material which would tend to remain collapsed, or other type of one-way valve. The valve will allow the cap to be worn for extended periods of time, by enabling menstrual and other bodily fluids to pass through the cap.

Figure 8:
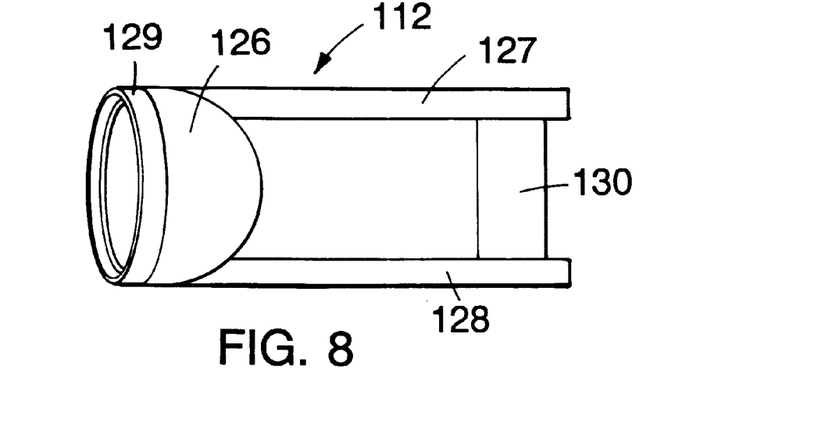
FIG. 8 shows a perspective view of a shell member according to one embodiment of the invention.

Referring to FIG. 8, an alternate configuration for shell member 112 is shown. Shell member 112 includes hemispherical shell 126, tubes 127 and 128 and spacer member 130 to support tubes 127 and 128 and maintain them in a stable spatial position.

Figure 9:
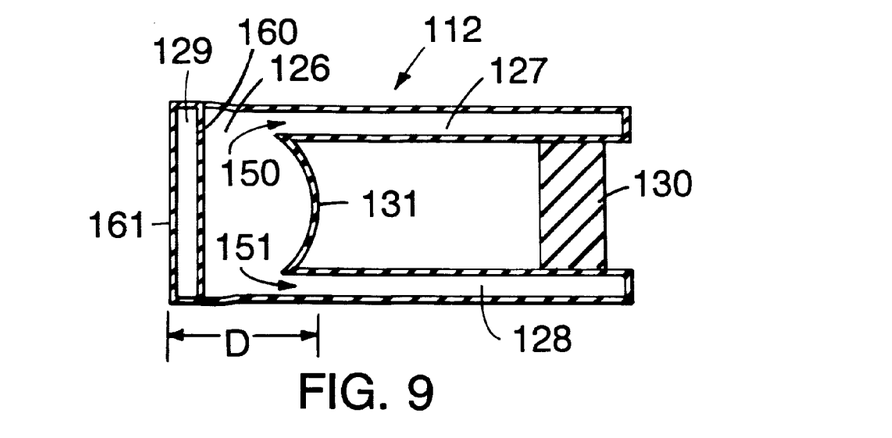
FIG. 9 shows a cross-sectional view of the shell member shown in FIG. 8.

Referring to FIG. 9, tubes 127 and 128 are in fluid communication with hemispherical shell 126, are substantially parallel to one another, and are disposed such that apertures 150 and 151 are approximately located at the 12 o'clock and 6 o'clock position on hemispherical shell 126. Hemispherical shell 126 and tubes 127 and 128 are preferably formed of a material which is translucent or transparent, and which the curable material to be used will not adhere to, e.g., ethylene vinyl acetate or cellulose acetate. Preferably, tubes 127 and 128 are approximately ½ mm thick and have an inner diameter equal to about 2 to 3 mm. Tubes 127 and 128 are sealingly connected to shell 126 and tube connector 130, e.g., by gluing or molding. Preferably the shell and tubes are molded together as a single integral unit.

Preferably the hemispherical shell 126 has a wall thickness of from about 1 to 3 mm, and has an inner diameter that is approximately 1 mm less than the inner diameter of base 129, forming annular groove 160. Preferably, annular rim 161 has an inner diameter that is 1 mm more than the inner diameter of base 129. Base 129 has an inner diameter equal to (for a pressure fit) or slightly smaller, e.g., about 1 to 3 mm smaller, than the outer diameter of the rim member 10 (FIG. 1). Thus, for the preferred rim member dimensions, the base 129 will have an outer diameter of from 27 to 50 mm. The depth of the hemispherical shell (dimension D) is preferably determined for each patient. The preferred depth of the shell is from 2 to 10 mm greater than the protrusion of the patient's cervix from the rim member when the rim member is in place, or typically from about 10 to 25 mm total depth.

Figure 10:
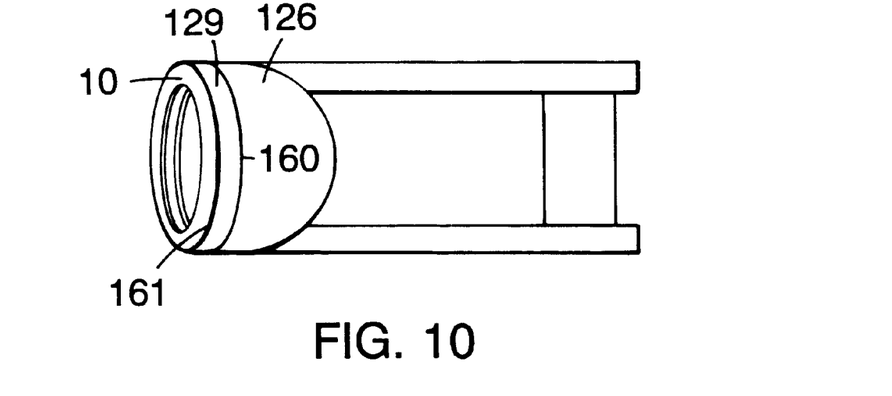
FIG. 10 is a perspective view of the rim member attached to the shell member.

As shown in FIG. 10, rim member 10 (from FIG. 1) is attached to hemispherical shell 126, e.g., by a pressure fit. In a preferred embodiment, annular groove 160 and annular rim 161 maintain the position of rim member 10 in shell member 112 when shell member 112 is placed on the patient's cervix. Specifically, annular groove 160 prevents rim member 10 from moving into hemispherical shell 126 and annular rim 161 prevents rim member 10 from moving forward, out of shell member 112.

A method of forming a cervical cap in situ, using the shell member shown in FIGS. 8–10, is shown in FIGS. 11a–11j. According to this method, the exocervix 38 is exposed (FIG. 11a), as described above for the method shown in FIGS. 4a–4d.

As shown in FIG. 1b, a shell member 112 and a rim member 10 of suitable size, e.g., which fits the exocervix 38 snugly, is selected, by trying different sizes, if necessary. Once a rim member of suitable size is found, the rim member 10 is preferably attached to the hemispherical shell 126 of shell member 112 prior to being applied to the exocervix 38, as shown. Alternatively, the rim member may be applied to the exocervix prior to the shell member being attached (not shown), as described for the method shown in FIGS. 4a–4d. The shell member/rim member assembly is then placed over the exocervix such that rim surface 18 (FIG. 1) is adjacent or near the fornices vaginae 40. The shell member/rim member assembly and/or cervix may be gently manipulated until this is achieved. Tubes 127 and 128 extend outside the vagina and beyond the speculum 37 so that a clinician has access to tube ends 131 and 132.

Figure 11A:
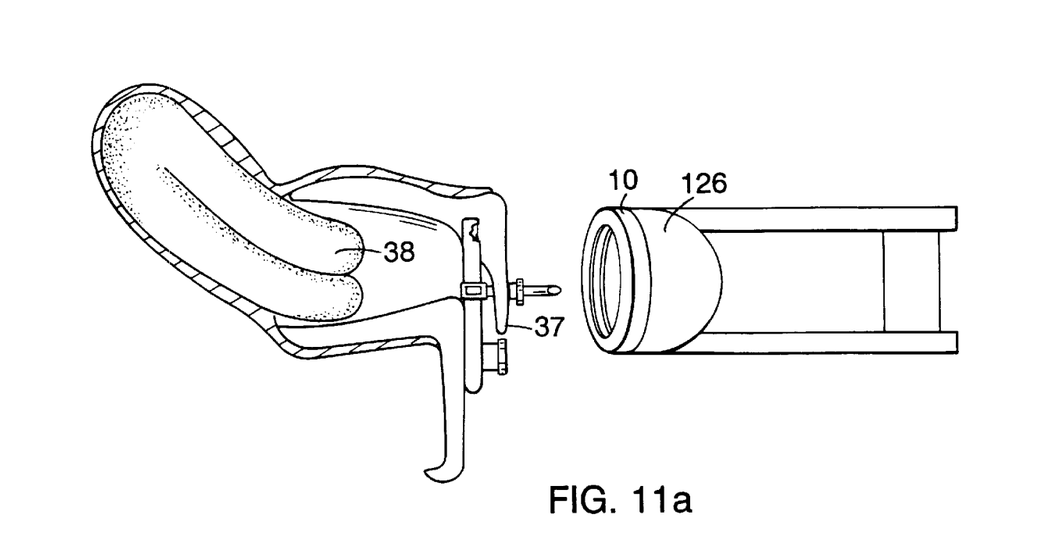
FIGS. 11a–11j show a method for forming a custom cervical cap according to an alternate embodiment of the invention.
Figure 11B:
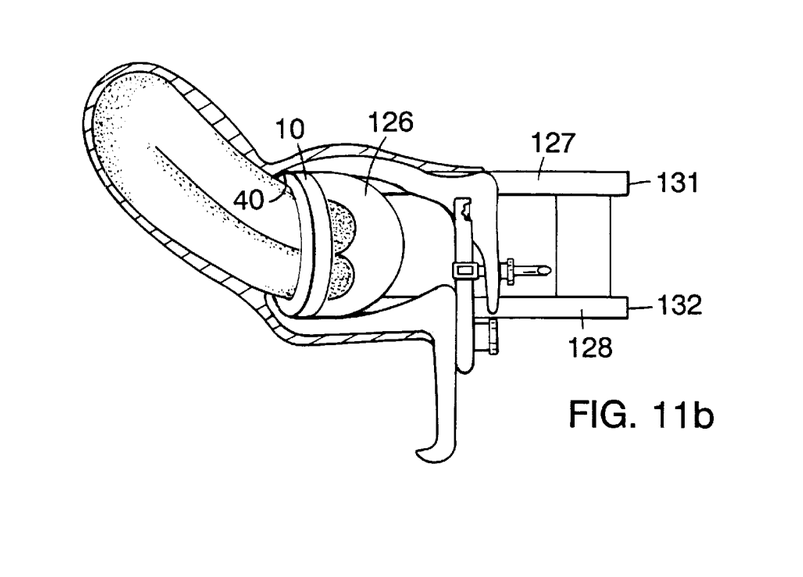
Figure 11C:
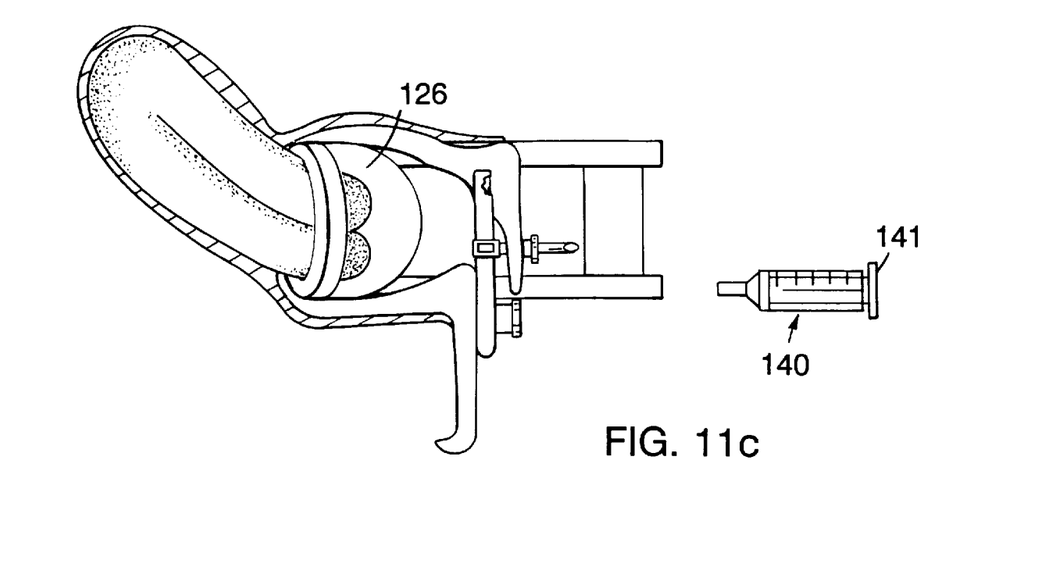
Figure 11D:
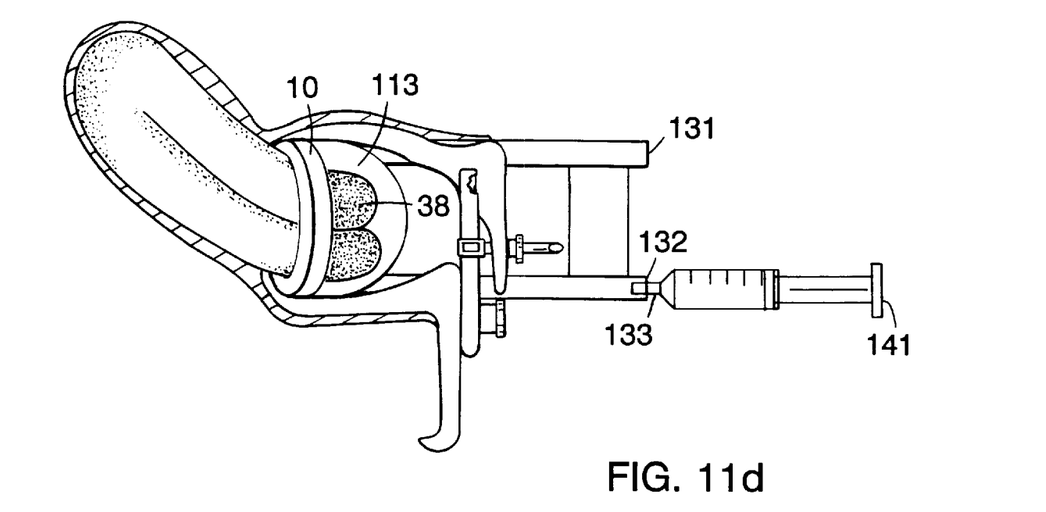
Figure 11E:
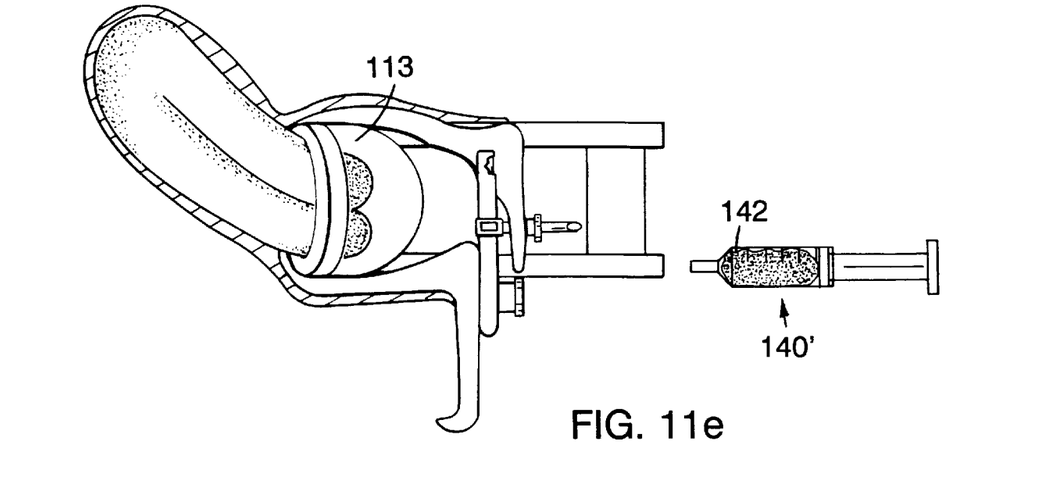
Figure 11F:
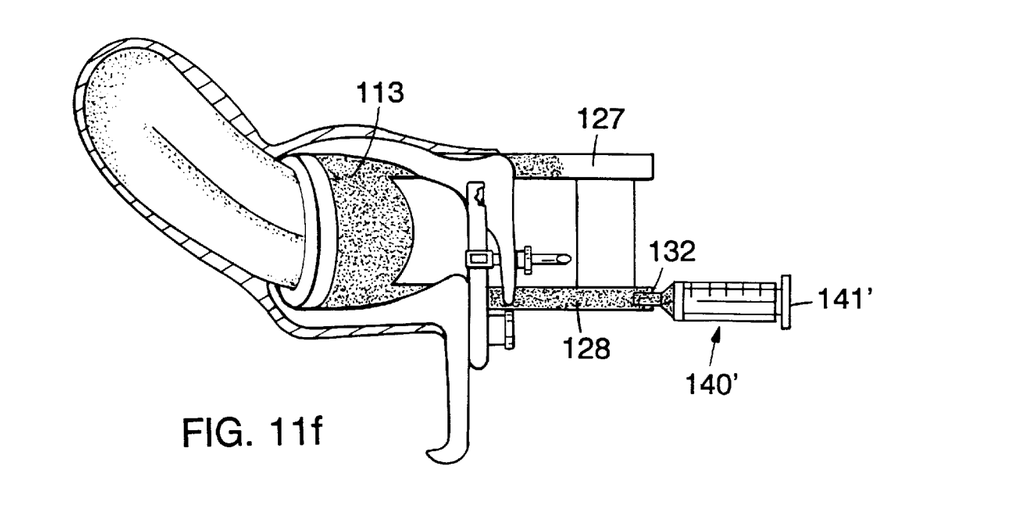

As shown in FIG. 11c, a syringe 140 is used to draw the cervix into the cavity defined by the hemispherical shell 126. To accomplish this, the syringe 140, with syringe handle 141 fully compressed, is placed in tube end 132 such that an air tight seal is formed between the inner surface of the tube and syringe tip 133. A seal to prevent air flow, e.g., a finger or a plug (not shown), is placed on tube end 131. The syringe handle 141 is then pulled back to create a vacuum which causes the patient's cervix to be drawn into cavity 113 and rim member 10 to be positioned around the patient's exocervix 38 (FIG. 11d). The syringe 140 and seal are then removed from tube ends 132 and 131 respectively. Curable material 142 in syringe 140', which can be the same syringe used to draw the vacuum, is dispensed into cavity 113 (FIG. 11e) by inserting syringe 140' into tube end 132 and compressing syringe handle 141' to force curable material 142 through tube 128 into cavity 113. The degree to which the cavity is filled can be determined by observing the output of curable material in translucent tube 127. To insure that cavity 113 is completely filled, curable material is injected into tube end 132 until the clinician sees material enter tube 127. If a nontranslucent tube is used, the clinician can insure that cavity 113 is completely filled by inserting curable material through tube 128 until it comes out of tube 127. The placement of tubes 127 and 128 at approximately the 12 o'clock and 6 o'clock positions on shell member 126 helps to ensure that no air pockets may be formed within cavity 113.

Figure 11G:
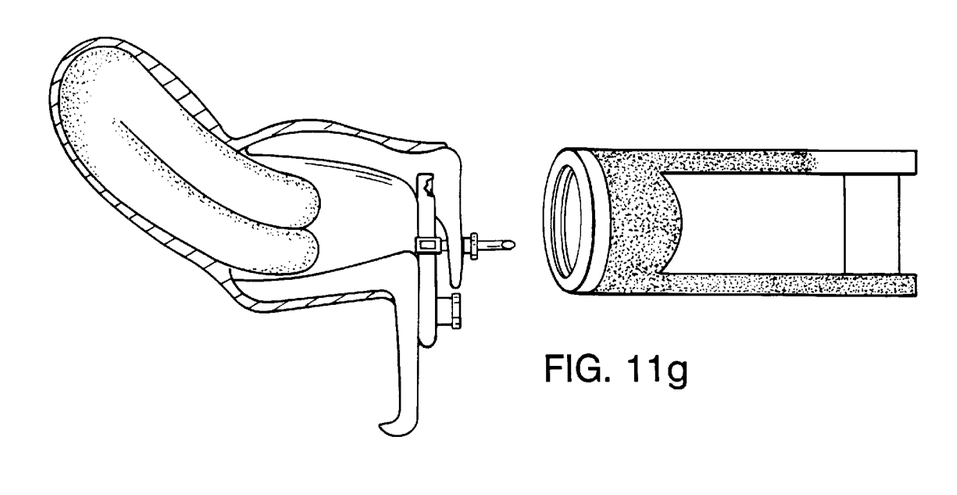
Figure 11H:
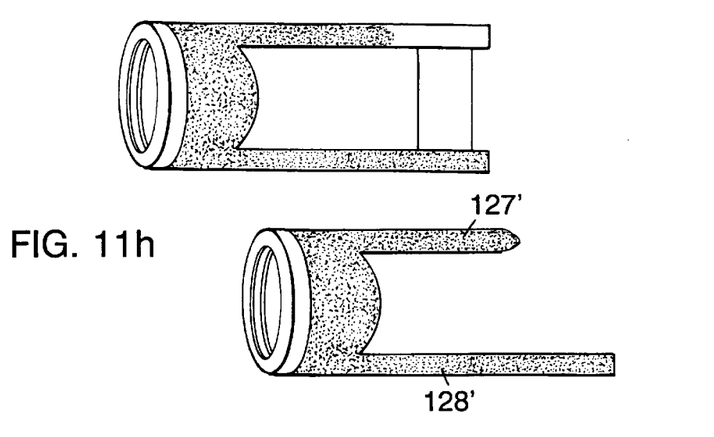
Figure 11I:
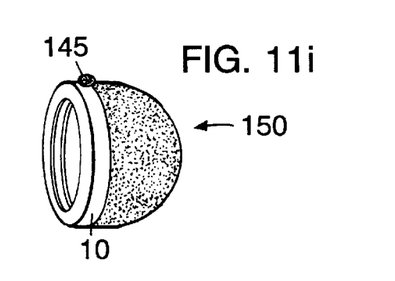
Figure 11J:
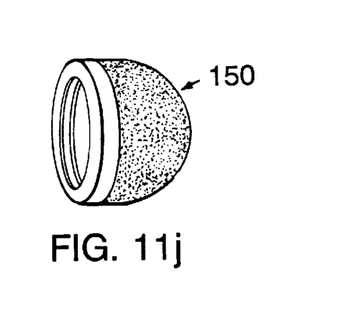

After the curable material has been allowed to harden, typically from about 5 to 15 minutes, depending upon the setting time of the material used, the entire assembly (rim, shell, tubes, and cured material) is removed together (FIG. 11g). The shell member is removed from the cured material (FIG. 11h), and tails 127' and 128' are preferably removed from cap 150 (FIG. 11i). A locator 145 is then positioned on rim member 10 at the twelve o'clock position, or any other position identified to the patient, so that the cap 150 may be correctly positioned on the exocervix by the patient during use. The position of locator 45 may be marked immediately after removing shell member 112.

Figure 12:
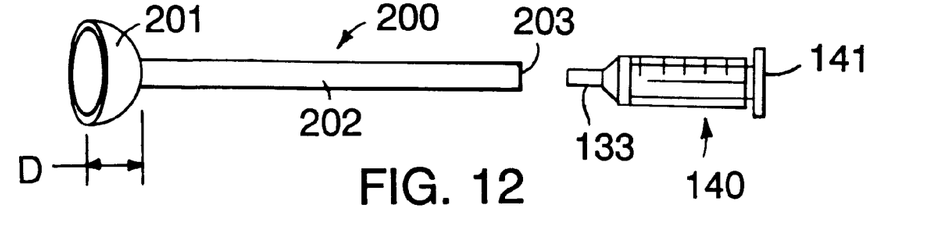
FIG. 12 shows a perspective view of a cervical plunger according to one embodiment of the invention.

As shown in FIG. 12, a cervical plunger 200 may be used by a clinician, in any of the above mentioned methods, to initially position the patient's cervix prior to forming a cervical cap. A cervical plunger 200 includes plunger member 201 and tube member 202. Tube member 202 is sealingly connected to and in fluid communication with plunger member 201 and extends outwardly from the plunger member 201 a sufficient distance so that it may be accessed by the clinician from outside the patient's body. Preferred dimensions of plunger member 201 are approximately as follows: inner diameter=5 to 15 mm, depth D=10 to 20 mm. Preferably plunger member 201 is made of a flexible, resilient material which can maintain a vacuum seal while moving and positioning the cervix, e.g., silicone rubber.

A method of positioning a cervix, according to a preferred embodiment, is shown in FIG. 12. The exocervix (not shown) is exposed, as described for the method shown in FIGS. 4a–4d. Cervical plunger 200 is placed on the exocervix such that the perimeter of plunger member 201 is in contact with the exocervix (not shown). Syringe 140 is used to create a vacuum between the exocervix and the plunger member so that the exocervix may be positioned by the clinician by moving cervical plunger 200. To accomplish this, the syringe 140, with syringe handle 141 fully compressed, is placed in tube end 203 such that an air tight seal is formed between the inner surface of the tube and syringe tip 133. The syringe handle 141 is then pulled back to create a vacuum causing plunger member 201 and the exocervix (not shown) to be sealingly connected. The clinician may then position the exocervix by manipulating the cervical plunger 200. When the exocervix is properly positioned, the syringe 140 is removed from tube end 203 to eliminate the vacuum seal. The cervical plunger may then be removed from the patient.

Figure 13:
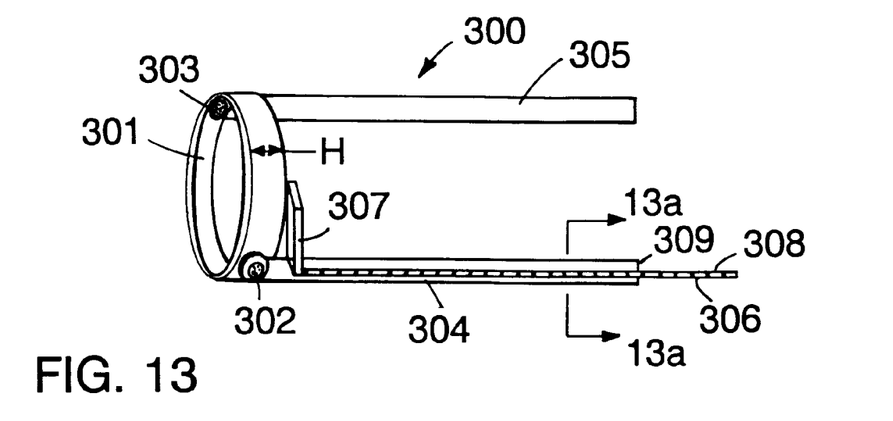
FIG. 13 shows a perspective view of a ring gauge according to one embodiment of the invention.

As shown in FIG. 13, a ring gauge 300 may be used by a clinician, in any of the above mentioned methods, to initially size the rim member 10 (FIG. 1) and shell member 12 (FIG. 2) or shell member 112 (FIG. 8). Ring gauge 300 includes a plurality of ring members 301, and a pair of handles 304, 305 which are adapted to be removably and rotatably secured to a selected ring member, e.g., with snaps 302 and 303 as shown, approximately 180° apart on the ring member. Rotatable attachment is preferred, as it enables the ring member to be moved to a position which allows the gauge to be inserted into the patient with minimal discomfort. Ring members 301 have differing inner diameters which are sized to fit the range of exocervix diameters which are commonly encountered in clinical practice, typically from 20 to 35 mm. The height of each ring member 301 (dimension H in FIG. 13) preferably corresponds to the height of rim member 10.

Figure 14:
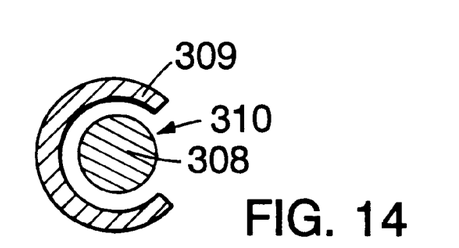

Gauge 300 further includes measuring member 306, which is slidably retained by handle 304, e.g., within a slotted lumen or a channel 310 in handle 304 (FIG. 14), and measuring stop 307, which extends from an end of measuring member 306, forming a 90 degree angle with the long axis of the measuring member. When ring member 301 and handles 304 and 305 are in the positions shown in FIG. 13, measuring member 306 may be positioned, by sliding it within lumen 310, such that measuring stop touches ring member 301 and is in the same plane as ring member 301. In this position, the indication scale 308 at handle end 309 reads zero. As measuring member 306 is moved in the opposite direction, away from ring member 301, the indication scale 308 indicates the distance from the ring member, preferably in 1 mm increments.

To measure a patient's exocervix, ring gauge 300 is inserted into the patient with ring member 301 rotated such that the diameter of ring member 301 and the long axes handles 304 and 305 are all in the same plane (not shown). Once ring gauge 300 is inserted into the patient, ring member 301 is rotated so that it is in a plane perpendicular to the plane formed by handles 304 and 305 (FIG. 13). Ring member 301 is then placed around the patient's cervix at the fornices vaginae (not shown) using handles 304 and 305 to position the ring member 301. If the ring member 301 is either too tight or too loose, the ring gauge 300 is removed from the patient and another ring member, of a different diameter, is attached to the ring gauge. These steps are repeated until the clinician determines that the ring member 301 is the right size for the patient. The size of the ring member corresponds to the size to be used for the rim member 10 (FIG. 1). When the right size for the ring member 301 is found, the clinician insures that the ring member is placed around the patient's cervix at the fornices vaginae and is positioned straight, such that the ring member 301 is in a plane perpendicular to the handles 304 and 305. The clinician then slides measuring member 306 within handle 304 until measuring stop 307 touches the apex of the patient's exocervix (not shown). The clinician reads the indication scale 308 at tube end 309 to determine the depth of the exocervix. Shell member 12 or 112 is then selected such that the depth of the shell member is 2 to 10 mm greater than the depth of the exocervix.

Other embodiments are within the claims. For example, in the embodiment in which the shell member includes an aperture, a single tube may be provided, extending from the shell member, to allow curable material to be delivered to the cavity from outside of the patient. Further, in the ring gauge, the handles may be removably attached to the ring member using any desired attachment technique.

What is claimed is:

1. A method of forming a cervical cap in situ, within a patient's body, comprising the sequential steps of:
   (a) positioning a snugly fitting rim member around the patient's exocervix so that a substantially ring-shaped surface of the rim member is exposed and faces towards the opening of the patient's vagina;
   (b) applying a curable material over the exocervix, without applying a shell to the rim, such that the curable material bonds to said exposed substantially ring-shaped surface of the rim member and covers the surface of the exocervix; and
   (c) allowing said curable material to harden so that, with the rim member, it forms a cervical cap.

2. A method of claim 1 wherein the curable material is applied in step (b) by providing a shell member having an aperture, filling the shell member with an excess of the curable material, and mounting the shell member on the rim member.

3. A method of claim 1 further comprising the step of, after the curable material has hardened, removing the cap, formed by the rim and curable material, from the patient's body.

4. A method of claim 3 further comprising the step of applying additional curable material to the outer surface of the hardened curable material after the cap is removed from the patient's body.

5. A method of claim 4 wherein said additional curable material is applied by placing a shell member, partially filled with curable material and having an aperture so that excess material can escape, over the outer surface of the cap.

6. A method of forming a cervical cap in situ, within a patient's body, comprising the steps of:
   (a) placing a snugly fitting rim member around a patient's exocervix, said rim member including one or more ridges on its inner surface to securely grip the exocervix;
   (b) mounting a shell member, having a plurality of tubes extending therefrom, onto said rim member such that the rim member, shell member and exocervix define a cavity and the tubes are in fluid communication with the cavity;
   (c) drawing a vacuum through one of the tubes to draw the patient's cervix into said cavity;
   (d) applying a curable material through one of the tubes to substantially fill the cavity;
   (e) allowing said curable material to harden and bond to the rim member so that said rim member and curable material define a cervical cap; and
   (f) removing said shell member from said rim member.

7. A method of claim 6 wherein said tubes are of sufficient length to allow them to be accessible from outside the patient's body.

8. A method of claim 6 wherein the shell member has two tubes extending therefrom.

9. A method of claim 6 wherein a stabilizer is used to support and maintain the tubes in a stable, spaced position.

10. A method of claim 6 further comprising the steps of, after the curable material has hardened, removing the assembly defined by the rim member, the shell member and the curable material from the patient, removing the shell member from the hardened curable material, and removing the portions of the hardened curable material which hardened in the tubes.

11. A method of claim 1 further comprising the step of placing a locator on said rim member to enable the patient to properly position the cervical cap.

12. A method of claim 6 wherein the shell member is mounted onto the rim member prior to placing the rim member on the exocervix.

13. A method of claim 6 wherein the shell member is translucent.

14. A method of claim 1 wherein said rim member includes a plurality of circumferential ridges on its inner surface to enable it to securely grip the exocervix.

15. A method of forming a cervical cap in situ, within a patient's body, comprising the sequential steps of:
   (a) positioning a snugly fitting ring-shaped rim member around the patient's exocervix;
   (b) mounting a shell member, having an aperture, onto the rim member such that the rim member, shell member and exocervix define a cavity;
   (c) applying a curable material over the exocervix, such that the curable material bonds to the rim and covers the surface of the exocervix;
   (d) allowing said curable material to harden so that, with the ring-shaped rim member, it forms a cervical cap; and
   (e) removing the shell from the rim member.

16. The method of claim 1 further comprising providing a valve in the cervical cap to allow egress of fluid from the uterus while preventing ingress of fluids.

17. The method of claim 6 further comprising providing a valve in the cervical cap to allow egress of fluid from the uterus while preventing ingress of fluids.

18. The method of claim 16 further comprising providing a valve in the cervical cap to allow egress of fluid from the uterus while preventing ingress of fluids.

19. The method of claim 1 wherein said ring-shaped rim member includes one or more ridges on its inner surface to securely grip the exocervix.

20. The method of claim 16 wherein said ring-shaped rim member includes one or more ridges on its inner surface to securely grip the exocervix.

21. The method of claim 1 further comprising measuring the circumference of the patient's exocervix prior to step (a).

22. The method of claim 6 further comprising measuring the circumference of the patient's exocervix prior to step (a).

23. The method of claim 15 further comprising measuring the circumference of the patient's exocervix prior to step (a).

24. The method of claim 1 further comprising (d) attaching a valve, constructed to allow egress of fluid from the uterus while preventing ingress of sperm, to a portion of the cervical cap to allow said egress of fluid.

25. The method of claim 6 further comprising (g) attaching a valve, constructed to allow egress of fluid from the uterus while preventing ingress of sperm, to a portion of the cervical cap to allow said egress of fluid.

26. The method of claim 16 further comprising (f) attaching a valve, constructed to allow egress of fluid from the uterus while preventing ingress of sperm, to a portion of the cervical cap to allow said egress of fluid.

27. A method of forming a cervical cap in situ, within a patient's body, comprising:
   (a) positioning a-snugly fitting rim member around the patient's exocervix, said rim member including one or more ridges on its inner surface to securely grip the exocervix;
   (b) applying a curable material over the exocervix so that the curable material bonds to the rim member;
   (c) allowing the curable material to harden so that, with the rim member, it forms a cervical cap; and
   (d) providing the cervical cap with a valve constructed to allow egress from the cervical cap of fluid from the uterus, through the valve, while preventing ingress of sperm into the cervical cap.

28. The method of claim 27 wherein the providing step includes molding the valve into the curable material.

29. The method of claim 27 wherein the providing step includes forming an aperture in the cervical cap after the curable material has hardened, placing the valve in the aperture, and attaching the valve to the cap in an impermeable manner.

30. The method of claim 27 wherein the valve is a flutter valve.

* * * * *